United States Patent [19]

Martin

[11] Patent Number: 4,749,406
[45] Date of Patent: Jun. 7, 1988

[54] QUINOLINE DERIVATIVES AND COMPOSITIONS THEREOF FOR THE PROTECTION OF CULTIVATED PLANTS

[75] Inventor: Henry Martin, Basel, Switzerland

[73] Assignee: Ciba-Geigy Corporation, Ardsley, N.Y.

[21] Appl. No.: 660,195

[22] Filed: Oct. 12, 1984

[30] Foreign Application Priority Data

Oct. 18, 1983 [CH] Switzerland .................. 5647/83

[51] Int. Cl.⁴ .................. A01N 43/42; C07D 215/26; C07D 215/28
[52] U.S. Cl. .................. 71/94; 546/178
[58] Field of Search .................. 546/178; 71/95, 94

[56] References Cited

U.S. PATENT DOCUMENTS

| | | | |
|---|---|---|---|
| 2,661,277 | 12/1953 | Mowry et al. | 546/178 |
| 3,131,509 | 5/1964 | Hoffmann | 47/1 |
| 3,351,525 | 0/1967 | Hodel | 546/178 X |
| 3,564,768 | 2/1971 | Hoffmann | 47/57.6 |
| 3,702,759 | 11/1972 | Hoffmann | 71/77 |
| 3,719,466 | 3/1973 | Ahle | 71/88 |
| 3,749,566 | 7/1973 | Hoffmann | 71/100 |
| 4,269,775 | 5/1981 | Szczrpanski | 260/340.7 |

FOREIGN PATENT DOCUMENTS

| | | | |
|---|---|---|---|
| 0086750 | 8/1983 | European Pat. Off. | 71/94 |
| 0094349 | 11/1983 | European Pat. Off. | 71/94 |
| 490419 | 2/1930 | Fed. Rep. of Germany | 546/178 |
| 2546845 | 7/1977 | Fed. Rep. of Germany | |
| 3000076 | 9/1981 | Fed. Rep. of Germany | |
| 1538541 | 4/1968 | France | |
| 0145629 | 11/1980 | Japan | 546/178 |
| 760319 | 10/1956 | United Kingdom | |
| 989578 | 4/1965 | United Kingdom | |
| 1003478 | 9/1965 | United Kingdom | |
| 1355204 | 6/1974 | United Kingdom | |

OTHER PUBLICATIONS

Thompson et al., "New Growth Regulating Compounds, I. Summary of Growth . . . ", *Bot. Gazette*, [1946], 476–507.

Major et al., "N-Alkoxy-N-Alkyl(Aryloxy)Acetamides and Their . . . ", *J. Med. Pharm. Chem.*, 4, 317–326 (1961).

Aveschke et al., "Aryloxyalkylamidoximes á Potentialités . . . ", *Evr. J. Med. Chem.-Chim. Ther.*, 10, 463–9 (1975).

*Primary Examiner*—Glennon H. Hollrah
*Assistant Examiner*—D. B. Springer
*Attorney, Agent, or Firm*—Edward McC. Roberts; Irving M. Fishman

[57] ABSTRACT

There are used for the protection of cultivated plants against the harmful effects of agricultural chemicals quinoline derivatives of the formula

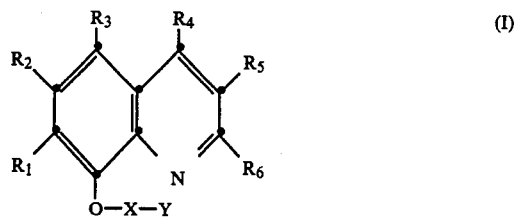

wherein $R_1$, $R_2$ and $R_3$ independently of one another are each hydrogen, halogen, nitro, cyano, alkyl, alkoxy or acyl, $R_4$, $R_5$ and $R_6$ independently of one another are each hydrogen, halogen or alkyl, X is an aliphatic, saturated or unsaturated, straight-chain or branched-chain hydrocarbon radical which has 1 to 12 carbon atoms and which can be interrupted by one or more hetero atoms or can be substituted by halogen, and Y is hydrogen, halogen, hydroxyl, alkoxy, alkenyloxy, alkynyloxy, a substituted amino group, an ammonio group, a cycloaliphatic radical, a heterocyclic radical which is substituted or substituted by alkyl having 1 to 4 carbon atoms, or is phenyl which is unsubstituted or substituted, or is aryloxy which is unsubstituted or substituted, or is benzyloxy which is unsubstituted or substituted, or is acyloxy, with the inclusion of the acid addition salts and metal complexes thereof; or there are used compositions which contain such derivatives. Also described are novel quinoline derivatives and the production thereof.

14 Claims, No Drawings

QUINOLINE DERIVATIVES AND COMPOSITIONS THEREOF FOR THE PROTECTION OF CULTIVATED PLANTS

The present invention relates to the use of quinoline derivatives for the protection of cultivated plants against the harmful effects of agricultural chemicals, to compositions containing these quinoline derivatives, to novel quinoline derivatives, and to the production of the novel quinoline derivatives.

With the use of agricultural chemicals, such as plant protection products, and especially herbicides, the cultivated plants can to a certain extent suffer damage depending on such factors as for example the dosage of agricultural chemical used and the mode of application, variety or type of cultivated plant, nature of the soil and climatic conditions, for example: duration of exposure to light, temperature and rainfall. It is thus known for example that herbicides from the most varied classes of substances, such as triazines, urea derivatives, carbamates, thiolcarbamates, haloacetanilides and halophenoxyacetic acids, and from other classes too, can, when applied in effective amounts, damage to some degree the cultivated plants which are supposed to be protected against the disadvantageous action of undesirable plant growth. In order to overcome this problem, there have already been suggested various substances which are capable of specifically antagonising the harmful action of a herbicide on the cultivated plants, that is to say, capable of protecting the cultivated plants without at the same time noticeably affecting the herbicidal action against the weeds to be controlled. It has however been shown that the suggested antidotes frequently have only a narrow field of action, that is, a specific antidote is suitable often only for application on individual varieties of cultivated plants, and/or for the protection of the cultivated plants against individual herbicidal substances or classes of substances.

The British Patent Specification No. 1,277,557 describes for instance the treatment of seeds or shoots of wheat and sorghum with certain oxamic acid esters and amides for protection against an attack by "ALACHLOR" (N-methoxymethyl-N-chloroacetyl-2,6-diethylaniline). In the German Offenlegungsschriften Nos. 1,952,910 and 2,245,471, and also in the French Patent Specification No. 2,021,611, there are suggested antidotes for treating cereal, maize and rice seeds for the purpose of protecting these against the harmful effect of herbicidally active thiolcarbamates. According to the German Patent Specification No. 1,567,075 and the U.S. Pat. No. 3,131,509, hydroxyaminoacetanilides and hydantoins are used for protecting cereal seeds against carbamates.

The direct pre- or post-emergence treatment of specific productive plants with antidotes, as antagonists of certain classes of herbicides, on a cultivated area of land is described in the German Offenlegungsschriften Nos. 2,141,586 and 2,218,097, and also in the U.S. Pat. No. 3,867,444.

Furthermore, according to the German Offenlegungsschrift No. 2,402,983, maize plants can be effectively protected against damage by chloroacetanilides by supplying the soil with an N-disubstituted dichloroacetamide as an antidote.

In addition, according to European Patent Application No. 11,047, it is possible to use alkoximinobenzyl cyanides, the alkoxy group of which is substituted, inter alia, by an acetalised carbonyl group, as active ingredients for the protection of cultivated plants against the harmful action of herbicides of various classes of substances.

The use of quinoline derivatives in the therapeutic field as starting products for producing therapeutic active substances, for promoting the growth of animals, as plant-growth inhibitors or as herbicides is moreover described for example in the U.S. Pat. No. 4,176,185, in the British Patent Specification Nos. 760,319, 989,578, 1,003,477 and 1,003,478, in the Swiss Patent Spec. No. 408,007, in the German Offenlegungsschrift No. 2,546,845, in Areschka, A. et. al., Eur. J. Med. Chem.-Chimica Therapeutica, September–October 1975-10, No. 5, 463–469, in Major R. T. et al., J. Med. Pharm. Chem. 4, 317–326, 1961, and in Thompson, H. E., Botan. Gaz. 107. 476–507, 1946.

It has now been found that, surprisingly, a group of quinoline derivatives are excellently suitable for protecting cultivated plants against the harmful effects of agricultural chemicals, for example plant protection products, in particular herbicides. These quinoline derivatives are therefore designated in the following as antidotes or 'safeners'.

Quinoline derivatives which are suitable for the protection of cultivated plants against the harmful effects of agricultural chemicals correspond to the formula I

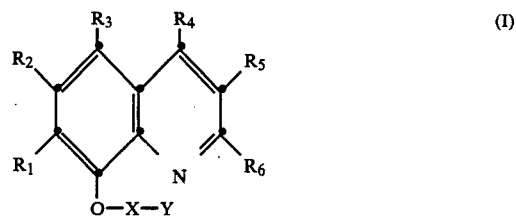

wherein
- $R_1$, $R_2$ and $R_3$ independently of one another are each hydrogen, halogen, nitro, cyano, alkyl, alkoxy or acyl,
- $R_4$, $R_5$ and $R_6$ independently of one another are each hydrogen, halogen or alkyl,
- X is an aliphatic, saturated or unsaturated, straight-chain or branched-chain hydrocarbon radical which has 1 to 12 carbon atoms and which can be interrupted by one or more hetero atoms or can be substituted by halogen, and
- Y is hydrogen, halogen, hydroxyl, alkoxy, alkenyloxy, alkynyloxy, a substituted amino group, an ammonio group, a cycloaliphatic radical, a heterocyclic radical which is unsubstituted or substituted by alkyl having 1 to 4 carbon atoms, or is phenyl which is unsubstituted or substituted, or is aryloxy which is unsubstituted or substituted, or is benzyloxy which is unsubstituted or substituted, or is acyloxy, with the inclusion of the acid addition salts and metal complexes thereof.

When optically isomeric compounds of the formula I exist, there is meant, within the scope of the present invention, both the optically pure isomers and the isomeric mixtures.

In the compounds of the formula I, halogen is fluorine, chlorine, bromine or iodine, especially chlorine, bromine and iodine.

The alkoxy group present as the substituent Y, and the alkyl and alkoxy groups denoted by $R_1$, $R_2$, $R_3$, $R_4$, $R_5$ and $R_6$, can be straight chain or branched-chain, and advantageously contain 1 to 8, preferably 1 to 4, and in particular 1 to 3, carbon atoms. Example of such substituents are: methyl, ethyl, n-propyl, isopropyl, n-pentyl, n-hexyl, n-heptyl, n-octyl, and isomers thereof, and also methoxy, ethoxy, isopropoxy, n-propoxy, butoxy, pentyloxy or hexyloxy.

Acyl groups are preferably alkylcarbonyl groups, in particular those having 1 to 6 carbon atoms and preferably 1 to 3 carbon atoms. These acyl groups also preferably from the acyl moiety of the acyloxy group. To be mentioned in this respect are for example the propionyloxy group and the acetoxy group.

Forming the substituent group —X—Y are, when Y is hydrogen, saturated or unsaturated, straight-chain or branched-chain hydrocarbons, which can be interrupted by one or more hetero atoms, for example oxygen. Examples of such hydrocarbon radicals are: methyl, ethyl, n-propyl, isopropyl, n-butyl, isobutyl, sec-butyl, tert-butyl, allyl, butenyl, methallyl, dimethylallyl, chloroallyl, propargyl, n-pentyl, isopentyl, n-hexyl, n-heptyl, n-octyl and n-dodecyl, and isomers thereof.

When Y has a meaning other than hydrogen, X denotes for example the hydrocarbon radicals mentioned in the foregoing for —X—Y less one hydrogen atom, for example methylene, ethylene, n-propylene, n-butylene, and isomers thereof.

As an alkenyloxy group or alkynyloxy group, Y is in particular one having 3 to 6, preferably 3 or 4, carbon atoms, for example allyloxy or propargyloxy.

In the case of the unsaturated hydrocarbon radicals bound by way of oxygen, the multiple bond is preferably separated from the oxygen atom by at least one carbon atom not participating in the multiple bond.

By a substituted amino group Y is preferably meant an amino group which is substituted by one or two alkyl groups each having 1 to 4 carbon atoms, for example dimethylamino or diethylamino.

An ammonio group is in particular a group of the formula —$N^{\oplus}R_aR_bR_c.Q^{\ominus}$, wherein $R_a$, $R_b$ and $R_c$ are preferably alkyl having 1 to 4 carbon atoms, for example methyl, or one of the substituents $R_a$, $R_b$ and $R_c$ can also be benzyl, and $Q^{\ominus}$ is an anion of an organic or inorganic acid, for example hydrochloric acid.

A cycloaliphatic radical is especially a cycloalkyl ring having 3 to 6 carbon atoms, for example cyclopropyl and cyclohexyl.

As a heterocyclic radical, Y denotes in particular saturated, 5- or 6-membered, heterocyclic rings having one or two oxygens atoms or a nitrogen atom, which are unsubstituted or substituted by alkyl having 1 to 4 carbon atoms, for example methyl. Examples of such heterocyclic rings are: piperidino, tetrahydrofuranyl, such as tetrahydrofuran-2-yl, dioxanyl, such as 1,3-dioxan-2-yl, and dioxolanyl unsubstituted or substituted by alkyl having 1 to 4 carbon atoms, such as 1,3-dioxolan-2-yl, 1,3-dioxolan-4-yl and 2-methyl-1,3-dioxolan-4-yl.

The aryl moiety of the aryloxy group is preferably an unsubstituted or substituted phenyl group.

In the compounds of the formula I, aromatic rings, which are present as substituents or as part of a substituent, can for their part be substituted, for example by halogen, alkoxy having 1 to 4 carbon atoms or alkyl having 1 to 4 carbon atoms, which is unsubstituted or mono- or poly-substituted by halogen, for example fluorine. Examples of such substituted aromatic radicals are: chlorophenyl, chlorophenoxy, methylphenoxy, methoxyphenoxy, p-chlorobenzyloxy, p-fluorobenzyloxy, p-methoxybenzyloxy and m-(trifluoromethyl)-benzyloxy.

Suitable salt formers are organic and inorganic acids. Examples of organic acids are acetic acid, trichloroacetic acid, oxalic acid, benzenesulfonic acid and methanesulfonic acid. And examples of inorganic acids are hydrochloric acid, hydrobromic acid, hydriodic acid, sulfuric acid, phosphoric acid, phosphorous acid and nitric acid.

Metal-complex formers which are suitable are for example elements of the 3rd and 4th main group, such as aluminium, tin and lead, and also of the 1st to 8th subgroup, for example chromium, manganese, iron, cobalt, nickel, zirconium, zinc, copper, silver and mercury. The subgroup elements of the 4th period are preferred.

Particularly suitable for application according to the invention are compounds of the formula I which belong to the compound groups listed in the following:

(a) compounds of the formula I in which $R_1$, $R_2$, $R_3$, $R_4$, $R_5$ and $R_6$ have the meanings defined for formula I, and X and Y together form an aliphatic, saturated or unsaturated hydrocarbon radical, including the acid addition salts and metal complexes thereof;

(b) compounds of the formula I in which $R_1$, $R_2$, $R_3$, $R_4$, $R_5$ and $R_6$ have the meanings defined for formula I, and X and Y together form an aliphatic saturated hydrocarbon radical, including the acid addition salts and metal complexes thereof;

(c) compounds of the formula I in which $R_1$, $R_2$, $R_3$, $R_4$, $R_5$ and $R_6$ have the meanings defined for formula I, and X and Y together form an aliphatic unsaturated hydrocarbon radical, including the acid addition salts and metal complexes thereof;

(d) compounds of the formula I in which $R_3$ is halogen, $R_1$, $R_2$, $R_4$, $R_5$ and $R_6$ have the meanings defined for formula I, and X and Y together form the n-octyl radical, including the acid addition salts and metal complexes thereof;

(e) compounds of the formula I in which $R_3$ is chlorine, $R_1$, $R_2$, $R_4$, $R_5$ and $R_6$ have the meanings defined for formula I, and X and Y together form the n-octyl radical, including the acid addition salts and metal complexes thereof;

(f) compounds of the formula I in which $R_3$ is halogen, $R_1$, $R_2$, $R_4$, $R_5$ and $R_6$ have the meanings defined for the formula I, and X and Y together form the 2-butenyl radical, including the acid addition salts and metal complexes thereof;

(g) compounds of the formula I in which $R_3$ is chlorine, $R_1$, $R_2$, $R_4$, $R_5$ and $R_6$ have the meanings defined for the formula I, and X and Y together form the 2-butenyl radical, including the acid addition salts and metal complexes thereof;

(h) compounds of the formula I in which $R_3$ is chlorine, $R_1$, $R_2$, $R_4$, $R_5$ and $R_6$ are hydrogen, and X and Y together form the n-octyl radical, including the acid addition salts and metal complexes thereof;

(i) compounds of the formula I in which $R_3$ is chlorine, $R_1$, $R_2$, $R_4$, $R_5$ and $R_6$ are hydrogen, and X and Y together form the 2-butenyl radical, including the acid addition salts and metal complexes thereof;

(k) compounds of the formula I in which $R_1$, $R_2$, $R_3$, $R_4$, $R_5$ and $R_6$ have the meanings defined for the formula I, X is methylene, and Y is phenyl which is unsubstituted or substituted, a dioxolane radical, a dioxane radical or a tetrahydrofuran radical, including the acid addition salts and metal complexes thereof;

(l) compounds of the formula I in which $R_1$, $R_2$, $R_3$, $R_4$, $R_5$ and $R_6$ have the meanings defined for the formula I, X is methylene, and Y is a dioxolane radical, a dioxane radical or a tetrahydrofuran radical, including the acid addition salts and metal complexes thereof;

(m) compounds of the formula I in which $R_3$ is halogen, $R_1$, $R_2$, $R_4$, $R_5$ and $R_6$ are hydrogen, X is methylene, and Y is a dioxolane radical, a dioxane radical or a tetrahydrofuran radical, including the acid addition salts and metal complexes thereof;

(n) compounds of the formula I in which $R_3$ is chlorine, $R_1$, $R_2$, $R_4$, $R_5$ and $R_6$ are hydrogen, X is methylene, and Y is a dioxolane radical, a dioxane radical or a tetrahydrofuran radical, including the acid addition salts and metal complexes thereof;

(o) compounds of the formula I in which $R_3$ is chlorine, $R_1$, $R_2$, $R_4$, $R_5$ and $R_6$ are hydrogen, X is methylene, and Y is a dioxolane radical, including the acid addition salts and metal complexes thereof;

(p) compounds of the formula I in which $R_3$ is chlorine, $R_1$, $R_2$, $R_4$, $R_5$ and $R_6$ are hydrogen, X is methylene, and Y is a dioxane radical, including the acid addition salts and metal complexes thereof;

(q) compounds of the formula I in which $R_3$ is chlorine, $R_1$, $R_2$, $R_4$, $R_5$ and $R_6$ are hydrogen, X is methylene, and Y is a tetrahydrofuran radical, including the acid addition salts and metal complexes thereof;

(r) compounds of the formula I in which $R_1$, $R_2$, $R_3$, $R_4$, $R_5$ and $R_6$ are hydrogen, and X and Y together form an aliphatic, saturated or unsaturated hydrocarbon radical, including the acid addition salts and metal complexes thereof;

(s) compounds of the formula I in which $R_1$, $R_2$, $R_3$, $R_4$, $R_5$ and $R_6$ are hydrogen, and X and Y together form the 2-butenyl radical, including the acid addition salts and metal complexes thereof;

(t) compounds of the formula I in which $R_1$, $R_2$, $R_3$, $R_4$, $R_5$ and $R_6$ are hydrogen, X is methylene, and Y is a dioxolane radical, a dioxane radical or a tetrahydrofuran radical, including the acid addition salts and metal complexes thereof;

(u) compounds of the formula I in which $R_1$, $R_2$, $R_3$, $R_4$, $R_5$ and $R_6$ are hydrogen, X is methylene, and Y is a dioxolane radical, including the acid addition salts and metal complexes thereof;

(v) compounds of the formula I in which $R_1$, $R_2$, $R_3$, $R_4$, $R_5$ and $R_6$ are hydrogen, X is methylene, and Y is a dioxane radical, including the acid addition salts and metal complexes thereof;

(w) compounds of the formula I in which $R_1$, $R_2$, $R_3$, $R_4$, $R_5$ and $R_6$ are hydrogen, X is methylene, and Y is a tetrahydrofuran radical, including the acid addition salts and metal complexes thereof;

(x) compounds of the formula I in which $R_1$, $R_2$, $R_3$, $R_4$, $R_5$ and $R_6$ have the meanings defined for the formula I, X is an aliphatic saturated hydrocarbon radical, and Y is halogen, hydroxyl, alkoxy, alkenyloxy, alkynyloxy, a substituted amino group, an ammonio group, a cycloaliphatic radical, a heterocyclic radical which is unsubstituted or substituted by alkyl having 1 to 4 carbon atoms, or is phenyl which is unsubstituted or substituted, or is aryloxy which is unsubstituted or substituted, or is benzyloxy which is unsubstituted or substituted, or is acyloxy, including the acid additions salts and metal complexes thereof;

(y) compounds of the formula I in which $R_3$ is chlorine, $R_1$, $R_2$, $R_4$, $R_5$ and $R_6$ have the meanings defined for the formula I, X is an aliphatic saturated hydrocarbon radical, and Y is halogen, hydroxyl, alkoxy, alkenyloxy, alkynyloxy, a substituted amino group, an ammonio group, a cycloaliphatic radical, a heterocyclic radical which is unsubstituted or substituted by alkyl having 1 to 4 carbon atoms, or is phenyl which is unsubstituted or substituted, aryloxy which is unsubstituted or substituted, benzyloxy which is unsubstituted or substituted, or acyloxy, including the acid addition salts and metal complexes thereof;

(z) compounds of the formula I in which $R_1$, $R_2$, $R_3$, $R_4$, $R_5$, $R_6$ and Y have the meanings defined for the formula I, and X is —$CH_2$—;

(a') compounds of the formula I in which $R_1$, $R_2$, $R_3$, $R_4$, $R_5$, $R_6$ and Y have the meanings defined for the formula I, and X is —$CH_2$—$CH_2$—;

(b') compounds of the formula I in which $R_1$, $R_2$, $R_3$, $R_4$, $R_5$, $R_6$ and Y have the meanings defined for the formula I, and X is —$CH_2$—$CH_2$—$CH_2$—;

(c') compounds of the formula I in which $R_1$, $R_2$, $R_3$, $R_4$, $R_5$, $R_6$ and Y have the meanings defined for the formula I, and X is —$CH_2$—CH=CH—$CH_2$—;

(d') compounds of the formula I in which $R_1$, $R_2$, $R_3$, $R_4$, $R_5$, $R_6$ and Y have the meanings defined for the formula I, and X is —$CH_2$—CH=CH—;

(e') compounds of the formula I in which $R_1$, $R_2$, $R_4$ and $R_5$ are hydrogen, $R_3$ is hydrogen or chlorine, and $R_6$ is hydrogen or methyl, and the substituent group —X—Y is n-octyl, allyl, 2-butenyl, propargyl, 1,3-dioxolan-2-ylmethyl, 1,3-dioxan-2-ylmethyl or tetrahydrofuran-2-ylmethyl;

(a") compounds in which $R_1$ is hydrogen, chlorine or bromine, $R_2$, $R_4$ and $R_5$ are hydrogen, $R_3$ is hydrogen, chlorine, bromine or nitro, $R_6$ is hydrogen or methyl, and (i) X is a $C_1$–$C_4$-alkylene radical or a $C_2$–$C_3$-alkenyl radical which is unsubstituted or substituted by chlorine, and Y is chlorine, 2-propenyloxy, dimethylamino, diethylamino, benzyldimethylammonio chloride, 1,3-dioxolanyl, methyl-1,3-dioxolanyl, 1,3-dioxanyl, furyl, piperidino, phenyl, chlorophenyl, phenoxy, methylphenoxy, benzyloxy or acetoxy, or (ii) Y is hydrogen, and X and Y together are butyl, octyl, 2-propenyl, chloro-2-propenyl, 2-butenyl or 2-propynyl, and of these in particular those compounds in which $R_1$ is hydrogen, chlorine or bromine, $R_2$, $R_4$ and $R_5$ are hydrogen, $R_3$ is hydrogen, chlorine, bromine or nitro, $R_6$ is hydrogen or methyl and (i) X is methylene and Y is 1,3-dioxolan-2-yl, or (ii) X is 2-chloro-2-propenylene, and Y is chlorine, or (iii) Y is hydrogen, and X and Y together are n-butyl, n-octyl or 2-butenyl;

(b") compounds in which $R_1$ and $R_3$ independently of one another are each hydrogen or chlorine, $R_2$, $R_4$ and $R_5$ are hydrogen, $R_6$ is hydrogen or methyl, X is methylene, and Y is 1,3-dioxolan-2-yl, 1,3-dioxolan-4-yl, 2-methyl-1,3-dioxolan-4-yl, 1,3-dioxan-2-yl, 2-furyl, phenyl or 4-chlorophenyl;

(c") compounds in which $R_1$ and $R_3$ independently of one another are each hydrogen, chlorine or bromine, $R_2$, $R_4$, $R_5$ and $R_6$ are hydrogen, X is ethylene or trimethylene, and Y is 2-propenyloxy, dimethylamino, diethylamino, benzyldimethylammonio chloride, piperidino, phenoxy, 4-methylphenoxy, benzyloxy or acetoxy;

(d") compounds in which $R_1$, $R_2$, $R_4$, $R_5$ and $R_6$ are hydrogen, $R_3$ is chlorine, and (i) X is 2-propenylene and Y is phenyl, or (ii) X is butenylene and Y is chlorine;

(e") compounds in which $R_1$, $R_2$, $R_4$, $R_5$ and $R_6$ are hydrogen, $R_3$ is chlorine, and Y is hydrogen, and X and Y together are n-butyl, sec-butyl, 2-propenyl, 2-chloro-2-propenyl, 2-butenyl or 2-propynyl; and (f") compounds of the formula Ia embraced by the formula I

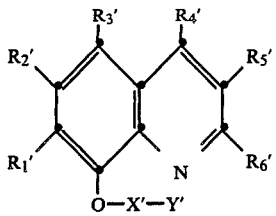

(Ia)

wherein

R$_1'$, R$_2'$ and R$_3'$ independently of one another are each hydrogen, halogen, nitro, cyano, alkyl, alkoxy or acyl, R$_4'$, R$_5'$ and R$_6'$ independently of one another are each hydrogen, halogen or alkyl, and the substituent group —X'—Y' is 2-butenyl, 1,3-dioxolan-2-ylmethyl, 1,3-dioxan-2-ylmethyl or tetrahydrofuran-2-ylmethyl.

Preferred individual compounds by virtue of their action are:
8-allyloxyquinoline,
8-(2-butenyloxy)-quinoline,
5-chloro-8-allyloxyquinoline,
5-chloro-8-propargyloxyquinoline,
5-chloro-8-(2-butenyloxy)-quinaldine,
8-octyloxyquinoline,
5-chloro-8-octyloxyquinoline,
8-octyloxyquinaldine,
5-chloro-8-octyloxyquinaldine,
8-(1,3-dioxolan-2-ylmethoxy)-quinoline,
5-chloro-8-(1,3-dioxolan-2-ylmethoxy)-quinoline,
8-(1,3-dioxan-2-ylmethoxy)-quinoline,
5-chloro-8-(1,3-dioxan-2-ylmethoxy)-quinoline,
5-chloro-8-(tetrahydrofuran-2-ylmethoxy)-quinoline,
and in particular
5-chloro-8-(2-butenyloxy)-quinoline.

The quinoline derivatives of the formula I have to an outstanding degree the property of protecting cultivated plants against the damaging effects of agricultural chemicals. Agricultural chemicals are for example: defoliating agents, desiccants, agents for protection against frost damage, and plant protection products, for example: insecticides, fungicides, bactericides, nematocides and especially herbicides. The herbicides can belong for example to one of the following classes of substances: triazines and triazinones; phenylureas, especially (3-(4-isopropylphenyl)-1,1-dimethylurea ("Isoproturon"); carbamates and thiocarbamates; haloacetanilides, in particular chloroacetanilides; chloroacetamides; halophenoxyacetic acid esters; diphenyl ethers, such as substituted phenoxyphenoxyacetic acid esters and -amides, and substituted phenoxyphenoxypropionic acid esters and -amides; substituted pyridyloxyphenoxyacetic acid esters and -amides, and substituted pyridyloxyphenoxypropionic acid esters and -amides, particularly 2-[4-(3,5-dichloropyridyl-2-oxy)-phenoxy]-propionic acid-2-propynyl ester; benzoic acid derivatives; nitroanilines; oxadiazolones; sulfonylureas; (4,5-dihydro-4-oxo-1H-imidazol-2-yl)-benzoic acid derivatives, -nicotinic acid derivatives and -quinolinecarboxylic acid derivatives, phosphates; and pyrazoles.

The following are specified as examples of substances which can be used:

triazines and triazinones: 2,4-bis(isopropylamino)-6-methylthio-1,3,5-triazine ("Prometryne"), 2,4-bis(ethylamino)-6-methylthio-1,3,5-triazine ("Simetryne"), 2-(1',2'-dimethylpropylamino)-4-ethylamino-6-methylthio-1,3,5-triazine ("Dimethametryne"), 4-amino-6-tert-butyl-4,5-dihydro-3-methylthio-1,2,4-triazin-5-one ("Metribuzin");

phenylureas: N-(3',4'-dimethylbenzyl)-N'-4-tolyl-urea (®Dimuron), and N-(3'-chloro-4'-isopropylphenyl)-N',N'-(3-methyl-pentamethylen-1,5-yl)-urea;

carbamates and thiocarbamates: N-(3',4'-dichlorophenyl)-propionanilide ("Propanil"), S-4-chlorobenzyl-diethylthiocarbamate ("Benthiocarb"), S-ethyl-N,N-hexamethylenethiocarbamate ("Molinate"), S-ethyl-dipropyl-thiocarbamate ("EPTC"), N,N-di-sec-butyl-S-benzyl-thiocarbamate (®Drepamon), S-(2,3-dichloroallyl)-di-isopropyl-thiocarbamate ("Di-allate") and 1-(propylthiocarbonyl)-decahydroquinaldine;

chloroacetanilides: 2-chloro-2',6'-diethyl-N-(2''-propyloxyethyl)-acetanilide ("Propalochlor"), 2-chloro-6'-ethyl-N-(2''-methoxy-1''-methylethyl)-acet-o-toluidide ("Metolachlor"), 2-chloro-2',6'-diethyl-N-(butoxymethyl)acetanilide ("butachlor"), 2-chloro-6'-ethyl-N-(ethoxymethyl)acet-o-toluidide ("Acetochlor"), 2-chloro-6'-ethyl-N-(2''-propoxy-1''-methylethyl)acet-o-toluidide, 2-chloro-2',6'-dimethyl-N-(2''-methoxy-1''-methylethyl)acetanilide, 2-chloro-2',6'-dimethyl-N-(2''-methoxyethyl)acetanilide ("Dimethachlor"), 2-chloro-2',6'-diethyl-N-(pyrazol-1-ylmethyl)acetanilide, 2-chloro-6'-ethyl-N-(pyrazol-1-ylmethyl)-acet-o-toluidide, 2-chloro-6'-ethyl-N-(3,5-dimethylpyrazol-1-ylmethyl)acet-o-toluidide, 2-chloro-6'-ethyl-N-(2''-butoxy-1''-methylethyl)acet-o-toluidide ("Metazolachlor"), 2-chloro-6'-ethyl-N-(2''-butoxyl-1''-(methylethyl)-acet-o-toluidide and 2-chloro-2'-trimethylsilyl-N-(butoxymethyl)-acetanilide;

chloroacetamides: N-[1-isopropyl-2-methylpropen-1-yl-(1)]-N-(2'-methoxyethyl)-chloroacetamide;

diphenyl ethers and nitrodiphenyl ethers: 2,4-dichlorophenyl-4'-nitrophenyl ether ("Nitrofen"), 2-chloro-1-(3'-ethoxy-4'-nitrophenoxy)-4-trifluoromethyl-benzene ("Oxyfluorfen"), 2',4'-dichlorophenyl-3-methoxy-4-nitrophenyl ether ("Chlormethoxynil"), 2-[4'-(2'',4''-dichlorophenoxy)phenoxy]propionic acid-methyl ester, N-(2'-phenoxyethyl)-2-[5'(2''-chloro-4''-trifluoromethylphenoxy)-phenoxy]-propionic acid amide;

benzoic acid derivatives: methyl-5-(2',4'-dichlorophenoxy)-2-nitrobenzoate ("Bifenox"), 5-(2'-chloro-4'-trifluoromethylphenoxy)-2-nitrobenzoic acid ("Acifluorfen") and 2,6-dichlorobenzonitrile ("Dichlobenil");

nitroanilines: 2,6-dinitro-N,N-dipropyl-4-trifluoromethylaniline ("Trifluralin") and N-(1'-ethylpropyl)-2,6-dinitro-3,4-xylidine ("Pendimethalin");

oxadiazolones: 5-tert-butyl-3-(2',4'-dichloro-5'-isopropoxyphenyl)-1,3,4-oxadiazol-2-one ("Oxadiazon");

phosphates: S-2-methylpiperidino-carbonylmethyl-O,O-dipropyl-phosphorodithioate ("Piperophos"); and pyrazoles: 1,3-dimethyl-4-(2',4'-dichlorobenzoyl)-5-(4'-tolylsulfonyloxy)-pyrazole.

The compounds of the formula I are particularly suitable for protecting cultivated plants against the harmful effects of herbicides of the formula H-I

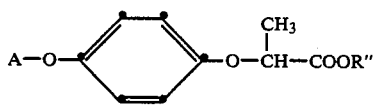

(H-I)

wherein
A is

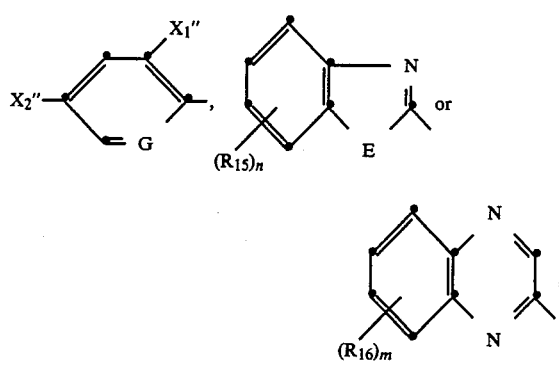

R″ is $C_1$–$C_4$-alkyl which is unsubstituted or substituted by $C_1$–$C_4$-alkoxy, or is $C_3$–$C_4$-alkenyl, $C_3$–$C_4$-alkynyl or

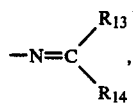

wherein $R_{13}$ is $C_1$–$C_4$-alkyl, $R_{14}$ is $C_1$–$C_4$-alkyl, or $R_{13}$ and $R_{14}$ together are $C_4$–$C_5$-alkylene,
$X_1″$ is hydrogen or halogen,
$X_2″$ is hydrogen, halogen or trifluoromethyl,
G is the fragment =N— or =CH—,
E is an oxygen or sulfur atom,
$R_{15}$ is halogen, $C_1$–$C_4$-alkyl or trifluoromethyl,
n is a number from 0 to 2,
$R_{16}$ is halogen, $C_1$–$C_4$-alkyl or trifluoromethyl, and
m is a number from 0 to 2.

To be emphasised is also the good protective action of compounds of the formula I on cultivated plants, particularly cereals, against the harmful effects of herbicides, such as diphenyl ether derivatives and substituted pyridyloxyphenoxypropionic acid esters, especially 2-[4-(3,5-dichloropyridyl-2-oxy)-phenoxy]-propionic acid-2-propynyl ester.

Cultivated plants which can be protected by quinoline derivatives of the formula I against agricultural chemicals are in particular those which are of importance in the foodstuffs and textile fields, for example cultivated millet, rice, maize, varieties of cereals (wheat, rye, barley, oats, and so forth), cotton, sugar beet, sugar cane and soya-bean.

A suitable process for protecting cultivated plants by the use of compounds of the formula I comprises treating cultivated plants, parts of these plants, or soils intended for the cultivation of the cultivated plants, before or after introduction of the vegetable material into the soil, with a compound of the formula I or with a composition containing such a compound. The treatment can be carried out before, simultaneously with or after the application of the agricultural chemicals. Parts of plants concerned are especially those which are capable of the new formation of a plant, for example seeds, fruits, stem parts and branches (cuttings), as well as roots, tubers and rhizomes.

The invention relates also to a process for the selective controlling of weeds in crops of cultivated plants, in which process the cultivated plants, parts of the cultivated plants, or cultivated areas for cultivated plants, are treated with a herbicide and a compound of the formula I, or with a composition containing this combination. The compositions which contain the herbicide/antidote combination likewise form subject matter of the present invention.

The weeds to be controlled can be both monocotyledonous and dicotyledonous.

Cultivated plants or parts of these plants to be protected are for example those mentioned in the foregoing. The cultivated areas concerned are those in which cultivated plants are already growing, or sown areas of land, and also the soil intended for the growing of cultivated plants.

The amount of antidote to be applied in proportion to the amount of agricultural chemical depends largely upon the type of application. In the case of a field treatment, which is carried out either with the use of a tank mixture or with a separate application of agricultural chemical and antidote, the employed ratio of antidote to agricultural chemical is as a rule from 1:100 to 10:1, preferably 1:5 to 8:1, and particularly 1:1.

With seed dressing and similar methods of application, however, the amounts of antidote required in proportion to the amounts of agricultural chemical applied per hectare of cultivated land are much smaller. There are used for seed dressing as a rule 0.1 to 10 g of antidote per kg of seed, preferably 1 to 2 g. When the antidote is applied shortly before sowing, with seed soaking, there are advantageously used antidote solutions containing the active ingredient at a concentration of 1 to 10,000 ppm, preferably 100 to 1000 ppm.

The compounds of the formula I can be used on their own or together with inert additives and/or the agricultural chemicals to be antagonised.

The present application relates therefore also to compositions which contain compounds of the formula I and inert additives and/or agricultural chemicals to be antagonised, especially plant protection agents, in particular herbicides.

For application, the compounds of the formula I, or combinations of compounds of the formula I with the agricultural chemicals to be antagonised, are advantageously used together with auxiliaries customarily employed in formulation practice, and are thus processed, in a known manner, for example into the form of emulsion concentrates, brushable pastes, directly sprayable or dilutable solutions, diluted emulsions, wettable powders, soluble powders, dusts or granulates, and also encapsulations in for example polymeric substances. The application processes, such as spraying, atomising, dusting, scattering, brushing or pouring, and likewise the type of composition, are selected to suit the objectives to be achieved and the given conditions.

The formulations, that is to say, the compositions or preparations containing the active ingredient of the formula I, or a combination of active ingredient of the formula I and agricultural chemicals to be antagonised, and optionally a solid or liquid additive are produced in a known manner, for example by the intimate mixing and/or grinding of the active ingredients with extenders, such as with solvents, solid carriers and optionally surface active compounds (tensides).

Suitable solvents are: aromatic hydrocarbons, preferably the fractions $C_8$ to $C_{12}$, such as xylene mixtures or substituted naphthalenes, phthalic esters, such as dibutyl- or dioctylphthalate, aliphatic hydrocarbons, such as cyclohexane or paraffins, alcohols and glycols, as well as ethers and esters thereof, such as ethanol, ethylene glycol, ethylene glycol momomethyl or -ethyl ethers, ketones such as cyclohexanone, strongly polar solvents, such as N-methyl-2-pyrrolidone, dimethyl sulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is also possible to add highly dispersed silicic acid or highly dispersed absorbent polymers. Suitable granulated adsorptive carriers are porous types, for example pumice, ground brick, sepiolite or bentonite; and suitable nonsorbent carriers are materials such as calcite or sand. There can also be used a great number of pregranulated materials of inorganic or organic nature, such as in particular dolomite or ground plant residues.

Suitable surface-active compounds are, depending on the nature of the active ingredient of the formula I to be formulated, and optionally also of the agricultural chemical to be antagonised, nonionic, cationic and/or anionic tensides having good emulsifying, dispersing and wetting properties. By 'tensides' are also meant mixtures of tensides.

Suitable anionic tensides are both so-called water-soluble soaps as well as water-soluble, synthetic, surface-active compounds.

Soaps which are applicable are the alkali metal, alkaline-earth metal or optionally substituted ammonium salts of higher fatty acids ($C_{10}$–$C_{22}$), for example the Na or K salts of oleic or stearic acid, or of natural fatty acid mixtures, which can be obtained for example from coconut oil or tallow oil. Also to be mentioned are the fatty acid-methyl-taurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Included among these are also the salts of sulfuric acid esters and sulfonic acids of fatty alcohol ethylene oxide adducts. The sulfonated benzimidazole derivatives preferably contain 2 sulfonic acid groups and a fatty acid group having 8–22 C atoms. Alkylarylsulfonates are for example the Na, Ca or triethanolamine salts of dodecylbenzenesulfonic acid, of dibutylnaphthalenesulfonic acid or of a naphthalenesulfonic acid-formaldehyde condensation product. Also suitable are corresponding phosphates, for example salts of the phosphoric ester of a p-nonylphenol-(4–14)-ethylene oxide adduct, or phospholipides.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols.

Further suitable nonionic tensides are the water-soluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Suitable also are fatty acid esters of polyoxyethylenesorbitan, such as polyoxyethylenesorbitan-trioleate.

In the case of the cationic tensides, they are in particular quaternary ammonium salts which contain as N-substituents at least one alkyl group having 8 to 22 C atoms and, as further substituents, lower, optionally halogenated alkyl, benzyl or lower hydroxyalkyl groups. The salts are preferably in the form of halides, methyl sulfates or ethyl sulfates, for example stearyltrimethylammonium chloride or benzyldi(2-chloroethyl)ethylammonium bromide.

The tensides customarily used in formulation practice are described, inter alia, in the following publications:

"Mc Cutcheon's Detergents and Emulsifiers Annual", MC Publishing Corp., Ridgewood, N.J., 1980, and Stache, H., "Tensid-Taschenbuch" (Tenside Pocketbook), Carl Hanser Verlag, Munich/Vienna, 1981.

The agrochemical preparations contain as a rule 0.1 to 99% by weight, especially 0.1 to 95% by weight, of active ingredient of the formula I or of a combination of active ingredient of the formula I and agricultural chemicals to be antagonised, 1 to 99.9% by weight, particularly 5 to 99.8% by weight, of a solid or liquid additive, and 0 to 25% by weight, especially 0.1 to 25% by weight, of a tenside.

Whereas commercial products are preferably in the form of concentrated compositions, the preparations employed by the end-user are as a rule diluted.

The compositions can also contain further additives, such as stabilisers, antifoaming agents, viscosity regulators, binders and adhesives, as well as fertilisers or other active substances for obtaining special effects.

For the use of compounds of the formula I, or of compositions containing them, for the protection of cultivated plants against the harmful effects of agricultural chemicals, various methods and techniques are applicable, such as those described in the following.

(i) Seed Dressing (a) Dressing of the seeds with an active ingredient of the formula I, formulated as a wettable powder, by shaking in a vessel until there is a uniform distribution over the surface of the seeds (dry dressing). The amount of active ingredient of the formula I used for this purpose is about 10 to 500 g (40 g to 2 kg of wettable powder) per 100 kg of seed.

(b) Dressing of the seeds with an emulsion concentrate of the active ingredient of the formula I according to method (a) (wet dressing).

(c) Dressing by immersion of the seed in liquor containing 50–3200 ppm of active ingredient of the formula I for 1 to 72 hours, and optionally subsequent drying of the seed (immersion dressing).

The dressing of the seed or the treatment of the germinated young seedlings is, in accordance with nature, the preferred method of application, because the treatment with the active ingredient is directed completely at the target growth. There are used as a rule 10 g to 500 g, preferably 50 to 250 g, of active ingredient per 100 kg of seed; however, depending on the method of treatment, which may render possible also the addition of other active substances or micronutrients, the stated limiting concentrations may be varied upwards or downwards (repeat dressing).

(ii) Application as Tank Mixture

A liquid preparation of a mixture of antidote and herbicide (quantitative ratio preferably between 10:1 and 1:10) is used, the applied amount of herbicide being 0.1 to 10 kg per hectare. This tank mixture is preferably applied before or immediately after sowing, or it is worked into the unsown soil to a depth of 5 to 10 cm.

(iii) Application into the Seed Furrow

The antidote is introduced, as an emulsion concentrate, wettable powder or granulate, into the open seed furrow, and, after the covering of the seed furrow in the normal manner, the herbicide is applied before the emergence of the plants.

(iv) Controlled Release of Active Ingredient

The active ingredient of the formula I is absorbed, in solution, onto mineral granular carriers or polymerised granulates (urea/formaldehyde), and the material is allowed to dry. A coating can if required be applied (coated granules), which enables the active ingredient to be released in controlled amounts over a specific period of time.

For a number of quinoline derivatives embraced by the formula I, processes for producing them are known, and also the use of these derivatives as bactericides and fungicides. The use of the quinoline derivatives of the formula I as safeners (antidotes) was however not known hitherto, and there is thus opened up a novel field of application.

Novel quinoline derivatives of the formula I form a part of the present application. Particularly worthy of mention are novel compounds of the formula Ia

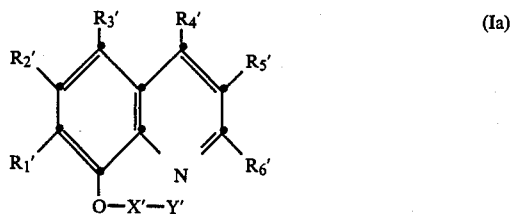

wherein
$R_1'$, $R_2'$ and $R_3'$ independently of one another are each hydrogen, halogen, nitro, cyano, alkyl, alkoxy or acyl,
$R_4'$, $R_5'$ and $R_6'$ independently of one another are each hydrogen, halogen or alkyl, and the substituent group —X'—Y' is 2-butenyl, 1,3-dioxolan-2-ylmethyl, 1,3-dioxan-2-ylmethyl or tetrahydrofuran-2-ylmethyl.

Compounds of the formula I especially worth mentioning are those which form the object of any one of the preferred compound groups: d, e, f, g, h, i, k, l, m, n, o, p, q, s, t, u, v and w.

Novel compounds of the formula I are produced by reacting a compound of the formula II

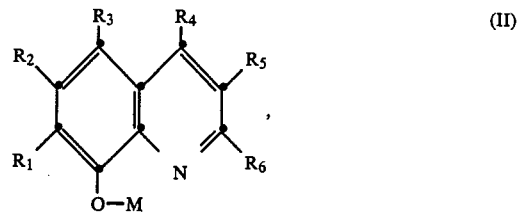

wherein $R_1$, $R_2$, $R_3$, $R_4$, $R_5$ and $R_6$ have the meanings defined for the formula I, and M is hydrogen, or an alkali metal or alkaline-earth metal atom, with a compound of the formula III

Z—X—Y (III), wherein X and Y have the meanings defined for the formula I, and Z is a detachable radical.

A detachable radical Z in the compound of the formula III is in particular a halogen atom or a methylsulfonyloxy, phenylsulfonyloxy or para-tolylsulfonyloxy group. Halogen in this case is fluorine, chlorine, bromine or iodine, preferably chlorine and bromine.

When in the compound of the formula II the symbol M is hydrogen and in the compound of the formula III the symbol Z denotes a halogen atom, the reaction is preferably performed in the presence of a customary proton acceptor. Furthermore, when in the compound of the formula III the symbol Z denotes a halogen atom, the addition of a small amount of alkali metal iodide acts catalytically.

The reaction is carried out advantageously in the presence of solvents which are inert to the reactants. Examples of such solvents are: hydrocarbons, such as benzene, toluene, xylene, petroleum ether or cyclohexane; ethers, for example diethyl ether, dipropyl ether, tetrahydrofuran, dioxane, dimethoxyethane or diethylene glycol/dimethyl ether; acid amides, for example dimethyl formamide, dimethylacetamide, 2-pyrrolidinone or hexamethylphosphoric acid triamide; or sulfoxides, for example dimethylsulfoxide.

Acid-binding agents which can be used are for example: hydroxides or alcoholates of alkali metals and alkaline-earth metals, or alkali carbonates or tertiary organic bases.

The reaction temperature are in general within a range of 0° to 200° C., particularly between 50° and 150° C.

The employed starting products are known, or they can be produced by methods analogous to known methods.

There can be produced in this manner compounds of preferred groups for example as follows:

Compounds of the group (g) are obtained by reacting a compound of the formula IV

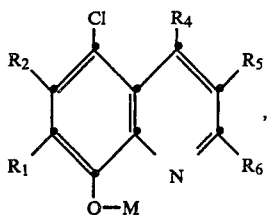

wherein $R_1$, $R_2$, $R_4$, $R_5$ and $R_6$ have the meanings defined for the formula I, and M is hydrogen or an alkali metal or alkaline-earth metal atom, with Z—CH$_2$—CH=CH—CH$_3$, wherein Z is a detachable radical.

Compounds of the group (h) are obtained by reacting a compound of the formula V

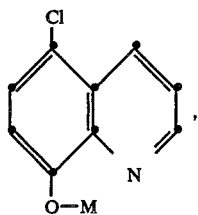

wherein M is hydrogen or an alkali metal or alkaline-earth metal atom, with Z—(CH$_2$)$_7$—CH$_3$, in which Z is a detachable radical.

Compounds of the group (i) are obtained by reacting a compound of the formula V

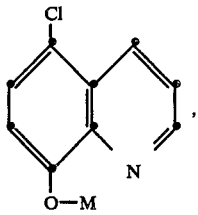

wherein M is hydrogen or an alkali metal or alkaline-earth metal atom, with Z—CH$_2$—CH=CH—CH$_3$, in which Z is a detachable radical.

Compounds of the group (o) are obtained by reacting a compound of the formula V

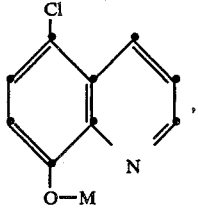

wherein M is hydrogen or an alkali metal or alkaline-earth metal atom, with

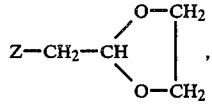

in which Z is a detachable radical.

Compounds of the group (p) are obtained by reacting a compound of the formula V

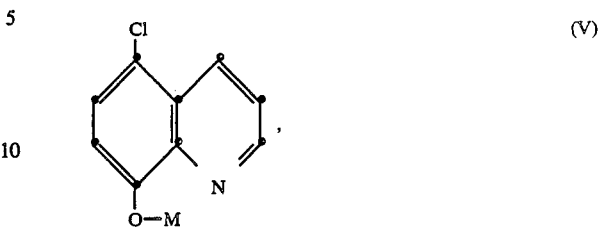

wherein M is hydrogen or an alkali metal or alkaline-earth metal atom, with

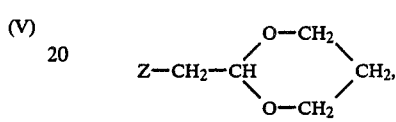

in which Z is a detachable radical.

Compounds of the group (q) are obtained by reacting a compound of the formula V

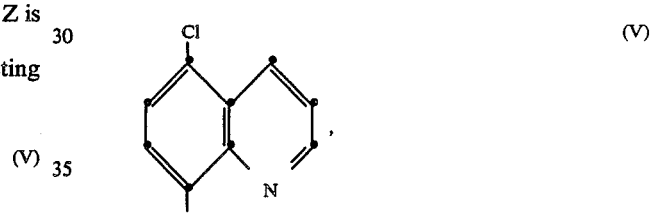

wherein M is hydrogen or an alkali metal or alkaline-earth metal atom, with

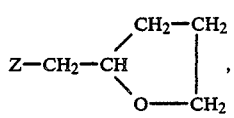

in which Z is a detachable radical.

Compounds of the group (s) are obtained by reacting a compound of the formula VI

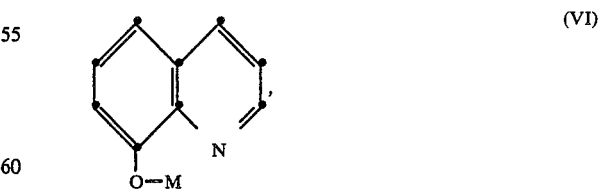

wherein M is hydrogen or an alkali metal or alkaline-earth metal atom, with Z—CH$_2$—CH=CH—CH$_3$, in which Z is a detachable radical.

Compounds of the group (u) are obtained by reacting a compound of the formula VI

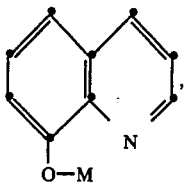

wherein M is hydrogen or an alkali metal or alkaline-earth metal atom, with

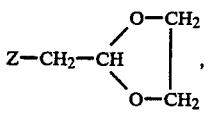

in which Z is a detachable radical.

Compounds of the group (v) are obtained by reacting a compound of the formula VI

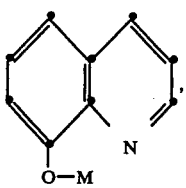

wherein M is hydrogen or an alkali metal or alkaline-earth metal atom, with

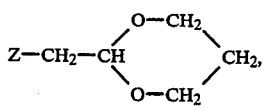

in which Z is a detachable radical.

Compounds of the group (w) are obtained by reacting a compund of the formula VI

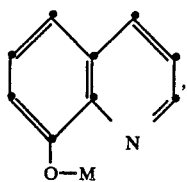

wherein M is hydrogen or an alkali metal or alkaline-earth metal atom, with

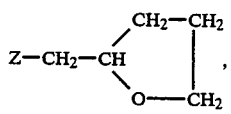

in which Z is a detachable radical.

The prior known quinoline derivatives can be produced by a procedure analogous to that described in the foregoing, or according to any one of the processes described in the literature stated in the following for producing 8-alkoxyquinolines: J. of General Chemistry of UdSSR 1952, Vol. 22, pp. 1263-1266; Acta Pharmaceutica Internationale Vol. II, No. 1-5, pp. 149-161; Arch. der Pharmazie 279 (1941), pp. 154-165; Bl (5) 12 (1945), pp. 866-870; J. Am Chem. Soc. 52, p. 4433 (1930); Helv. Chim. acta 27, p. 1736; Ber. 14, 2570; Ber. 49, 518; J.p. Chem. 93, 376.

The compounds can be produced also by a production process which has recently become known, namely the Phase-Transfer-Catalytic Process of Chin-Hsien et al., from Synthesis 1982, Mo. 10, pp. 858-861.

The 8-oxyquinolines and the substitution products thereof used as starting materials are known: 8-oxyquinoline, 8-oxyquinaldine, 5-chloro-8-oxyquinoline, 5-chloro-8-oxyquinaldine, 7-chloro-8-oxyquinoline, 7-chloro-8-oxyquinaldine, 5,7dichloro-8-oxyquinoline, 5-chloro-7-iodo-8-oxyquinoline, 5-bromo-8-oxyquinoline, 5,7-dibromoquinoline, and so forth. The production thereof is found in part in Beta Pharmaceutics Internationale Vol. II, No. 1-5, p. 153 (1951), Copenhagen. The production of 5-aceto-8-oxyquinoline and 5-ethyl-8-oxyquinoline is described in Arch. der Pharmazie 279 (1941) p. 154. Preferred starting materials are 8-oxyquinoline, 8-oxyquinaldine, 5-chloro-8-oxyquinoline and 5-chloro-8-oxyquinaldine.

PRODUCTION EXAMPLES FOR ACTIVE SUBSTANCES

Example 1

5-Chloro-8-(2-butenyloxy)-quinoline (compound No. 1)

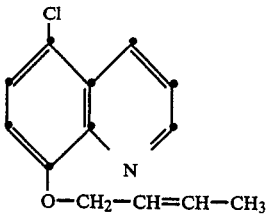

3.6 g (0.09 mol) of NaOH pellets are dissolved in 300 ml of water, and 300 ml of methylene chloride are added; there are subsequently added 10.8 g (0.06 mol) of 5-chloro-8-oxyquinoline, 16.2 g of 2-butenyl bromide (0.12 mol) and 0.5 g of tetra-n-butylammonium bromide, and the mixture is stirred for 5 hours at room temperature. The organic layer is separated, and the aqueous layer is extracted twice with methylene chloride. The organic solvents are combined and concentrated by evaporation. The residue is taken up in water and methylene chloride; the organic layer is then extracted by shaking three times with 2N NaOH, separated, dried with $Na_2SO_4$ and concentrated by evaporation; crude yield 15.5 g.

Dist. at 0.08-0.06 mbar, 122°-120° C.: 8.9 g, b.p. 123-131/0.06-0.08

| $C_{13}H_{12}Cl\ NO\ Mg\ 233.5$ | | | |
|---|---|---|---|
| calculated: | 66.81% C | found: | 67.0% C |
| | 5.18% H | | 5.6% H |
| | 6.0% N | | 5.6% N |

Example 2

8-(1,3-Dioxolan-2-ylmethoxy)-quinoline (compound No. 2)

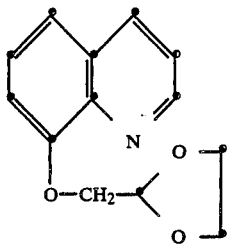

(compound No. 2)

36.6 g of potassium-8-quinoline oxide are finely ground, and heated in 120 ml of dimethyl sulfoxide at 45°–50° C. with stirring. After everything has dissolved, the solution is cooled, and 33.4 g of 2-bromomethyl-1,3-dioxolane are added at room temperature. The mixture is stirred at 60°–65° C. for 6 hours and subsequently concentrated by evaporation. The residue is taken up in water and methylene chloride; the organic layer is filtered through siliceous earth and then washed three times with water and diluted NaOH; it is afterwards washed neutral with water, dried with $Na_2SO_4$ and concentrated by evaporation.

Dist. at 0.1 mbar, 145°–150° C.: m.p. 60°–63° C., 12.9 g.

| | $C_{13}H_{13}O_3N$ Mg 231.25 | | |
|---|---|---|---|
| calculated: | 67.52% C | found: | 67.2% C |
| | 5.67% H | | 5.9% H |
| | 6.06% N | | 6.4% N |

5-Chloro-8-(1,3-dioxolan-2-ylmethoxy-quinoline

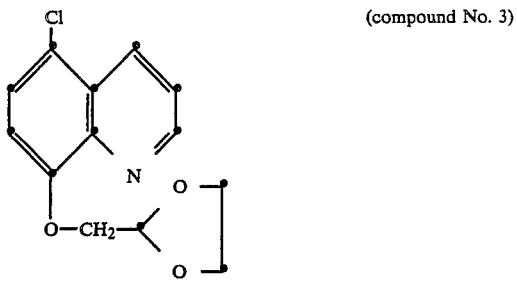

(compound No. 3)

is produced in the same manner.

There can be produced by methods analogous to those described in the foregoing also the following compounds of the formula I which are listed in Table 1 together with the compounds of the above Examples.

TABLE 1

| Comp. No. | $R_1$ | $R_2$ | $R_3$ | $R_4$ | $R_5$ | $R_6$ | X | Y | Physical constants |
|---|---|---|---|---|---|---|---|---|---|
| 1 | H | H | H | H | H | H | —CH₂—CH=CH—CH₂— | H | b.p. 123–127° C./ 0.06–0.08 mm |
| 2 | H | H | H | H | H | H | —CH₂— | (dioxolane) | m.p. 60–63° C. |
| 3 | H | H | Cl | H | H | H | —CH₂— | (dioxolane) | |
| 4 | H | H | H | H | H | H | —CH₂—CH=CH—CH₂— | H | b.p. 107–110° C./ 0.06 mm |
| 5 | H | H | H | H | H | H | —(CH₂)₈— | H | b.p. 163–164° C. 6,8 mm |
| 6 | H | H | Cl | H | H | H | —(CH₂)₈— | H | |
| 7 | H | H | H | H | H | CH₃ | —CH₂—CH=CH— | H | |
| 8 | H | H | H | H | H | CH₃ | —(CH₂)₈— | H | oil |
| 9 | H | H | H | H | H | H | —CH₂— | (dioxane) | |
| 10 | H | H | Cl | H | H | H | —CH₂— | (dioxane) | |
| 11 | H | H | H | H | H | H | —CH₂—C(Cl)=CH— | H | |
| 12 | H | H | H | H | H | H | —CH₂—C(Cl)=CH— | Cl | m.p. 105–106° C. |

TABLE 1-continued

| Comp. No. | R$_1$ | R$_2$ | R$_3$ | R$_4$ | R$_5$ | R$_6$ | X | Y | Physical constants |
|---|---|---|---|---|---|---|---|---|---|
| 13 | Cl | H | Cl | H | H | H | —CH$_2$—C(Cl)=CH— | Cl | m.p. 89–91° C. |
| 14 | Cl | H | Cl | H | H | H | —(CH$_2$)$_8$— | H | |
| 15 | Br | H | Br | H | H | H | —(CH$_2$)$_8$— | H | m.p. 41–43° C. |
| 16 | H | H | NO$_2$ | H | H | H | —(CH$_2$)$_4$— | H | m.p. 107–108,5° C. |
| 17 | Br | H | Br | H | H | H | —(CH$_2$)$_4$— | H | m.p. 61–63° C. |
| 18 | H | H | Cl | H | H | H | —CH$_2$— | 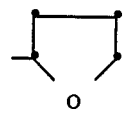 | |
| 19 | Cl | H | Cl | H | H | H | —CH$_2$— | 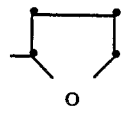 | |
| 20 | H | H | Cl | H | H | H | —CH$_2$— | 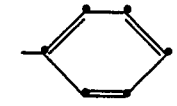 | |
| 21 | H | H | Cl | H | H | H | —CH$_2$— |  | |
| 22 | H | H | Cl | H | H | H | —CH$_2$— | 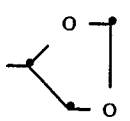 | |
| 23 | H | H | Cl | H | H | H | —CH$_2$— | 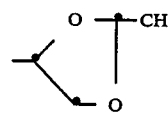 | |
| 24 | H | H | Cl | H | H | H | —CH$_2$—CH=CH— | 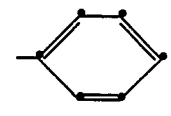 | |
| 25 | H | H | Cl | H | H | H | —CH$_2$—CH=CH—CH$_2$— | Cl | |
| 26 | H | H | H | H | H | H | —CH$_2$—CH$_2$— | 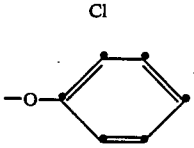 | |
| 27 | H | H | Cl | H | H | H | —CH$_2$—CH$_2$— | 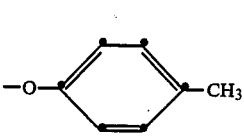 | |
| 28 | H | H | Cl | H | H | H | —CH$_2$—CH$_2$— | —O—CH$_2$—CH=CH$_2$ | |
| 29 | H | H | Cl | H | H | H | —CH(CH$_3$)—CH$_2$—CH$_2$— | H | |
| 30 | H | H | Cl | H | H | H | —CH$_2$—CH$_2$— | —N(CH$_3$)$_2$ 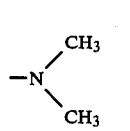 | |

TABLE 1-continued

| Comp. No. | R1 | R2 | R3 | R4 | R5 | R6 | X | Y | Physical constants |
|---|---|---|---|---|---|---|---|---|---|
| 31 | H | H | Cl | H | H | H | —CH2—CH2— | —N(C2H5)2 | |
| 32 | Cl | H | Cl | H | H | H | —CH2—CH2— | —N⁺(CH3)2(CH2—C6H5) ·Cl | |
| 33 | H | H | Cl | H | H | H | —CH2—CH2—CH2— | —N(piperidine) | |
| 34 | Cl | H | Cl | H | H | H | —CH2—CH2— | —N(C2H5)2 | |
| 35 | Br | H | Br | H | H | H | —CH2—CH2— | —N(CH3)2 | |
| 36 | H | H | H | H | H | CH3 | —CH2— | 1,3-dioxolan-2-yl (gem-dimethyl) | |
| 37 | H | H | Cl | H | H | CH3 | —CH2— | 1,3-dioxolan-2-yl (gem-dimethyl) | |
| 38 | H | H | Cl | H | H | CH3 | —CH2—CH=CH—CH2— | H | |
| 39 | Cl | H | H | H | H | CH3 | —CH2—CH=CH—CH2— | H | |
| 40 | H | H | Cl | H | H | H | —CH2—CH2— | —O—CO—CH3 | |
| 41 | H | H | Cl | H | H | H | —CH2—CH2—CH2— | —O—CH2—C6H5 | |
| 42 | Cl | H | Cl | H | H | H | —CH2— | 1,3-dioxolan-2-yl (gem-dimethyl) | |
| 43 | Cl | H | Cl | H | H | H | —CH2—CH=CH—CH2— | H | |
| 44 | H | H | H | H | H | H | —CH2—CH=CH— | H | |
| 45 | H | H | Cl | H | H | H | —CH2—CH=CH— | H | |
| 46 | H | H | Cl | H | H | H | —CH2—C≡C— | H | |
| 47 | H | H | Cl | H | H | CH3 | —(CH2)8— | H | |

FORMULATION EXAMPLES FOR LIQUID ACTIVE INGREDIENTS OF THE FORMULA I (%=PERCENT BY WEIGHT)

| 3. Emulsion concentrates | (a) | (b) | (c) |
|---|---|---|---|
| active ingredient from Table 1 | 25% | 40% | 50% |
| calcium dodecylbenzenesulfonate | 5% | 8% | 6% |
| castor oil-polyethylene glycol ether (36 mols of ethylene oxide) | 5% | — | — |
| tributylphenol-polyethylene glycol ether (30 mols of ethylene oxide) | — | 12% | 4% |
| cyclohexanone | — | 15% | 20% |
| xylene mixture | 65% | 25% | 20% |

Emulsions of any required concentration can be produced from concentrates of this type by dilution with water.

| 4. Solutions | (a) | (b) | (c) | (d) |
|---|---|---|---|---|
| active ingredient from Table 1 | 80% | 10% | 5% | 95% |
| ethylene glycol-monomethyl ether | 20% | — | — | — |
| polyethylene glycol M.W. 400 | — | 70% | — | — |
| N—methyl-2-pyrrolidone | — | 20% | — | — |
| epoxidised coconut oil | — | — | 1% | 5% |
| ligroin (boiling limits 160–190° C.) | — | — | 94% | — |

The solutions are suitable for application in the form of very fine drops.

| 5. Granulates | (a) | (b) |
|---|---|---|
| active ingredient from Table 1 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 6. Dusts | (a) | (b) |
|---|---|---|
| active ingredient from Table 1 | 2% | 5% |
| highly dispersed silicic acid | 1% | 5% |
| talcum | 97% | — |
| kaolin | — | 90% |

Ready-for-use dusts are obtained by the intimate mixing together of the carriers with the active ingredient.

FORMULATION EXAMPLES FOR SOLID ACTIVE INGREDIENTS OF THE FORMULA I (%=PERCENT BY WEIGHT)

| 7. Wettable powders | (a) | (b) | (c) |
|---|---|---|---|
| active ingredient from Table 1 | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7–8 mols of ethylene oxide) | — | 2% | — |
| highly dispersed silicic acid | 5% | 10% | 10% |
| kaolin | 62% | 27% | — |

The active ingredient is well mixed with the additives and the mixture is thoroughly ground in a suitable mill. Wettable powders which can be diluted with water to give suspensions of any required concentration are obtained.

| 8. Emulsion concentrate | |
|---|---|
| active ingredient from Table 1 | 10% |
| octylphenolpolyethylene glycol ether (4–5 mols of ethylene oxide) | 3% |
| calcium dodecylbenzenesulfonate | 3% |
| castor oil polyglycol ether (35 mols of ethylene oxide) | 4% |
| cyclohexanone | 30% |
| xylene mixture | 50% |

Emulsions of any required concentration can be obtained from this concentrate by dilution with water.

| 9. Dusts | (a) | (b) |
|---|---|---|
| active ingredient from Table 1 | 5% | 8% |
| talcum | 95% | — |
| kaolin | — | 92% |

Dusts ready for use are obtained by mixing the active ingredient with the carriers and grinding the mixture in a suitable mill.

| 10. Extruder granulate | |
|---|---|
| active ingredient from Table 1 | 10% |
| sodium lignin sulfonate | 2% |
| carboxymethylcellulose | 1% |
| kaolin | 87% |

The active ingredient is mixed and ground with the additives, and the mixture is moistened with water. This mixture is extruded and subsequently dried in a stream of air.

| 11. Coated granulate | |
|---|---|
| active ingredient from Table 1 | 3% |
| polyethylene glycol (M.W. 200) | 3% |
| kaolin | 94% |

The finely ground active ingredient is evenly applied, in a mixer, to the kaolin moistened with polyethylene glycol. Dustfree coated granules are obtained in this manner.

| 12. Suspension concentrate | |
|---|---|
| active ingredient from Table 1 | 40% |
| ethylene glycol | 10% |
| nonylphenolpolyethylene glycol ether (15 mols of ethylene oxide) | 6% |
| sodium lignin sulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the additives. There is thus obtained a suspension concentrate from which can be produced, by dilution with water, suspensions of any concentration required.

FORMULATION EXAMPLES FOR ACTIVE-INGREDIENT MIXTURES (LIQUID) [%=PERCENT BY WEIGHT]

| 13. Emulsion concentrates | (a) | (b) | (c) |
|---|---|---|---|
| active-ingredient mixture: antidote from Table 1 and a herbicide in the ratio 1:1 | 25% | 40% | 50% |
| calcium dodecylbenzenesulfonate | 5% | 8% | 6% |
| castor oil-polyethylene glycol ether (36 mols of ethylene oxide) | 5% | — | — |
| tributylphenol-polyethylene glycol ether (30 mols of ethylene oxide) | — | 12% | 4% |
| cyclohexanone | — | 15% | 20% |
| xylene mixture | 65% | 25% | 20% |

Emulsions of any required concentration can be produced from concentrates of this type by dilution with water.

| 14. Emulsion concentrates | (a) | (b) | (c) |
|---|---|---|---|
| active-ingredient mixture: antidote from Table 1 and a herbicide in the ratio of 1:3 | 25% | 40% | 50% |
| calcium dodecylbenzenesulfonate | 5% | 8% | 6% |
| castor oil-polyethylene glycol ether (36 mols of ethylene oxide) | 5% | — | — |
| tributylphenol-polyethylene glycol ether (30 mols of ethylene oxide) | — | 12% | 4% |
| cyclohexanone | — | 15% | 20% |
| xylene mixture | 65% | 25% | 20% |

Emulsions of any required concentration can be produced from concentrates of this type by dilution with water.

| 15. Emulsion concentrates | (a) | (b) | (c) |
|---|---|---|---|
| active-ingredient mixture: antidote from Table 1 and a herbicide in the ratio of 2:1 | 25% | 40% | 50% |
| calcium dodecylbenzenesulfonate | 5% | 8% | 6% |
| castor oil-polyethylene glycol ether (36 mols of ethylene oxide) | 5% | — | — |
| tributylphenol-polyethylene glycol (30 mols of ethylene oxide) | — | 12% | 4% |
| cyclohexanone | — | 15% | 20% |
| xylene mixture | 65% | 25% | 20% |

Emulsions of any required concentration can be produced from concentrates of this type by dilution with water.

| 16. Emulsion concentrates | (a) | (b) | (c) |
|---|---|---|---|
| active-ingredient mixture: antidote from Table 1 and 2-[4-(3,5-dichloro-pyridyl-2-oxy)-phenoxy]-propionic acid-2-propynyl ester in the ratio 1:1 | 25% | 40% | 50% |
| calcium dodecylbenzenesulfonate | 5% | 8% | 6% |
| castor oil-polyethylene glycol ether (36 mols of ethylene oxide) | 5% | — | — |
| tributylphenol-polyethylene glycol ether (30 mols of ethylene oxide) | — | 12% | 4% |
| cyclohexanone | — | 15% | 20% |
| xylene mixture | 65% | 25% | 20% |

Emulsions of any required concentration can be produced from concentrates of this type by dilution with water.

| 17. Emulsion concentrates | (a) | (b) | (c) |
|---|---|---|---|
| active-ingredient mixture: antidote from Table 1 and 2-[4-(3,5-dichloro-pyridyl-2-oxy)-phenoxy]-propionic acid-2-propynyl ester in the ratio of 1:3 | 25% | 40% | 50% |
| calcium dodecylbenzenesulfonate | 5% | 8% | 6% |
| castor oil-polyethylene glycol ether (36 mols of ethylene oxide) | 5% | — | — |
| tributylphenol-polyethylene glycol ether (30 mols of ethylene oxide) | — | 12% | 4% |
| cyclohexanone | — | 15% | 20% |
| xylene mixture | 65% | 25% | 20% |

Emulsions of any required concentration can be produced from concentrates of this type by dilution with water.

| 18. Solutions | (a) | (b) | (c) | (d) |
|---|---|---|---|---|
| active-ingredient mixture: antidote from Table 1 and a herbicide in the ratio of 1:4 | 80% | 10% | 5% | 95% |
| ethylene glycol-monomethyl ether | 20% | — | — | — |
| polyethylene glycol M.W. 400) | — | 70% | — | — |
| N—methyl-2-pyrrolidone | — | 20% | — | — |
| epoxidised coconut oil | — | — | 1% | 5% |
| ligroin (boiling limits 160–190° C.) | — | — | 94% | — |

The solutions are suitable for application in the form of very fine drops.

| 19. Solutions | (a) | (b) | (c) | (d) |
|---|---|---|---|---|
| active-ingredient mixture: antidote from Table 1 and a herbicide in the ratio of 5:2 | 80% | 10% | 5% | 95% |
| ethylene glycol-monomethyl ether | 20% | — | — | — |
| polyethylene glycol (M.W. 400) | — | 70% | — | — |
| N—methyl-2-pyrrolidone | — | 20% | — | — |
| epoxidised coconut oil | — | — | 1% | 5% |
| ligroin (boiling limits 160–190° C.) | — | — | 94% | — |

The solutions are suitable for application in the form of very small drops.

| 20. Solutions | (a) | (b) | (c) | (d) |
|---|---|---|---|---|
| active-ingredient mixture: antidote from Table 1 and a herbicide in the ratio of 1:1 | 80% | 10% | 5% | 95% |
| ethylene glycol-monomethyl ether | 20% | — | — | — |
| polyethylene glycol (M.W. 400) | — | 70% | — | — |
| N—methyl-2-pyrrolidone | — | 20% | — | — |
| epoxidised coconut oil | — | — | 1% | 5% |
| ligroin (boiling limits 160–190° C.) | — | — | 94% | — |

The solutions are suitable for application in the form of very fine drops.

| 21. Solutions | (a) | (b) | (c) | (d) |
|---|---|---|---|---|
| active-ingredient mixture: antidote from Table 1 and 2-[4-(3,5-dichloropyridyl-2-oxy)-phenoxy]-propionic acid-2-propynyl ester in the ratio of 1:1 | 80% | 10% | 5% | 95% |
| ethylene glycol-monomethyl ether | 20% | — | — | — |
| polyethylene glycol (M.W. 400) | — | 70% | — | — |
| N—methyl-2-pyrrolidone | — | 20% | — | — |
| epoxidised coconut oil | — | — | 1% | 5% |
| ligroin (boiling limits 160–190° C.) | — | — | 94% | — |

The solutions are suitble for application in the form of very small drops.

| 22. Solutions | (a) | (b) | (c) | (d) |
|---|---|---|---|---|
| active-ingredient mixture: antidote from Table 1 and 2-[4-(3,5-dichloropyridyl-2-oxy)-phenoxy]-propionic acid-2-propynyl ester in the ratio of 1:4 | 80% | 10% | 5% | 95% |
| ethylene glycol-monomethyl ether | 20% | — | — | — |
| polyethylene glycol (M.W. 400) | — | 70% | — | — |
| N—methyl-2-pyrrolidone | — | 20% | — | — |
| epoxidised coconut oil | — | — | 1% | 5% |
| ligroin (boiling limits 160–190° C.) | — | — | 94% | — |

The solutions are suitable for application in the form of very small drops.

| 23. Granulates | (a) | (b) |
|---|---|---|
| active-ingredient mixture: antidote from Table 1 and a herbicide in the ratio of 1:1 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 24. Granulates | (a) | (b) |
|---|---|---|
| active-ingredient mixture: antidote from Table 1 and 2-[4-(3,5-dichloro-pyridyl-2-oxy)-phenoxy]-propionic acid-2-propynyl ester in the ratio of 1:1 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 25. Dusts | (a) | (b) |
|---|---|---|
| active-ingredient mixture: antidote from Table 1 and a herbicide in the ratio of 1:1 | 2% | 5% |
| highly dispersed silicic acid | 1% | 5% |
| talcum | 97% | — |
| kaolin | — | 90% |

Ready-for-use dusts are obtained by the intimate mixing together of the carriers with the active ingredient.

FORMULATION EXAMPLES FOR ACTIVE-INGREDIENT MIXTURES (SOLID) (% = PERCENT BY WEIGHT)

| 26. Wettable powders | (a) | (b) | (c) |
|---|---|---|---|
| active-ingredient mixture: antidote from Table 1 and a herbicide in the ratio of 1:1 | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7–8 mols of ethylene oxide) | — | 2% | — |
| highly dispersed silicic acid | 5% | 10% | 10% |
| kaolin | 62% | 27% | — |

The active ingredient is well mixed with the additives and the mixture is thoroughly ground in a suitable mill. Wettable powders which can be diluted with water to give suspensions of any required concentration are obtained.

| 27. Wettable powders | (a) | (b) | (c) |
|---|---|---|---|
| active-ingredient mixture: antidote from Table 1 and a herbicide in the ratio of 1:4 | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7–8 mols of ethylene oxide) | — | 2% | — |
| highly dispersed silicic acid | 5% | 10% | 10% |
| kaolin | 62% | 27% | — |

The active ingredient is well mixed with the additives and the mixture is thoroughly ground in a suitable mill. Wettable powders which can be diluted with water to give suspensions of any required concentration are obtained.

| 28. Wettable powders | (a) | (b) | (c) |
|---|---|---|---|
| active-ingredient mixture: antidote from Table 1 and a herbicide in the ratio of 3:1 | 25% | 50% | 75% |
| sodium lignin sulfonate | 5% | 5% | — |
| sodium lauryl sulfate | 3% | — | 5% |
| sodium diisobutylnaphthalenesulfonate | — | 6% | 10% |
| octylphenolpolyethylene glycol ether (7–8 mols of ethylene oxide) | — | 2% | — |
| highly dispersed silicic acid | 5% | 10% | 10% |
| kaolin | 62% | 27% | — |

The active ingredient is well mixed with the additives and the mixture is thoroughly ground in a suitable mill. Wettable powders which can be diluted with water to give suspensions of any required concentration are obtained.

| 29. Emulsion concentrate | |
|---|---|
| active-ingredient mixture: antidote from Table 1 and a herbicide in the ratio of 1:1 | 10% |
| octylphenol polyethylene glycol ether (4–5 mols of ethylene oxide) | 3% |
| calcium dodecylbenzenesulfonate | 3% |
| castor oil-polyglycol ether (35 mols of ethylene oxide) | 4% |
| cyclohexanone | 30% |
| xylene mixture | 50% |

Emulsions of any required concentration are obtained from this concentrate by dilution with water.

| 30. Emulsion concentrate | |
|---|---|
| active-ingredient mixture: antidote from Table 1 and a herbicide in the ratio of 5:2 | 10% |
| octylphenol polyethylene glycol ether (4–5 mols of ethylene oxide) | 3% |
| calcium dodecylbenzenesulfonate | 3% |
| castor oil-polyglycol-ether (35 mols of ethylene oxide) | 4% |
| cyclohexanone | 30% |
| xylene mixture | 50% |

Emulsions of any required concentration are obtained from this concentrate by dilution with water.

| 31. Emulsion concentrate | |
|---|---|
| active-ingredient mixture: antidote from Table 1 and a herbicide in the ratio of 1:4 | 10% |
| octylphenol polyethylene glycol ether (4–5 mols of ethylene oxide) | 3% |
| calcium dodecylbenzenesulfonate | 3% |
| castor oil-polyglycol ether | 4% |

31. Emulsion concentrate

| | |
|---|---|
| (35 mols of ethylene oxide) | |
| cyclohexanone | 30% |
| xylene mixture | 50% |

Emulsions of any required concentration can be obtained from this concentrate by dilution with water.

32. Dusts

| | (a) | (b) |
|---|---|---|
| active-ingredient mixture: antidote from Table 1 and a herbicide in the ratio of 1:1 | 5% | 8% |
| talcum | 95% | — |
| kaolin | — | 92% |

Dusts ready for use are obtained by mixing the active ingredient with the carriers and grinding the mixture in a suitable mill.

33. Extruder granulate

| | |
|---|---|
| active-ingredient mixture: antidote from Table 1 and a herbicide in the ratio of 1:1 | 10% |
| sodium lignin sulfonate | 2% |
| carboxymethylcellulose | 1% |
| kaolin | 87% |

The active ingredient is mixed and ground with the additives, and the mixture is moistened with water. This mixture is extruded and subsequently dried in a stream of air.

34. Coated granulate

| | |
|---|---|
| active-ingredient mixture: antidote from Table 1 and a herbicide in the ratio of 1:1 | 3% |
| polyethylene glycol (M.W. 200) | 3% |
| kaolin | 94% |

The finely ground active ingredient is evenly applied, in a mixer, to the kaolin moistened with polyethylene glycol. Dustfree coated granules are obtained in this manner.

35. Suspension concentrate

| | |
|---|---|
| active-ingredient mixture: antidote from Table 1 and a herbicide in the ratio of 1:1 | 40% |
| ethylene glycol | 10% |
| nonylphenolpolyethylene glycol ether (15 mols of ethylene oxide) | 6% |
| sodium lignin sulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the additives. There is thus obtained a suspension concentrate from which can be produced, by dilution with water, suspensions of any concentration required.

36. Suspension concentrate

| | |
|---|---|
| active-ingredient mixture: antidote from Table 1 and a herbicide in the ratio of 1:4 | 40% |
| ethylene glycol | 10% |
| nonylphenolpolyethylene glycol ether (15 mols of ethylene oxide) | 6% |
| sodium lignin sulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the additives. There is thus obtained a suspension concentrate from which can be produced, by dilution with water, suspensions of any concentration required.

37. Suspension concentrate

| | |
|---|---|
| active-ingredient mixture: antidote from Table 1 and a herbicide in the ratio of 3:1 | 40% |
| ethylene glycol | 10% |
| nonylphenolpolyethylene glycol ether (15 mols of ethylene oxide) | 6% |
| sodium lignin sulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the additives. There is thus obtained a suspension concentrate from which can be produced, by dilution with water, suspensions of any concentration required.

BIOLOGICAL EXAMPLES

Example 38

Test with antidote and herbicide on wheat

Wheat seeds are sown in plastic pots each containing 0.5 liter of garden soil in a greenhouse. After the emergence of the plants up to the 2- to 3-leaf stage, the substance to be tested as antidote is applied together with the herbicide, 2-[4-(3,5-dichloropyridyl-2-oxy)-phenoxy]-propionic acid-2-propynyl ester, as a tank mixture. The applied amounts of antidote and herbicide correspond to 0.5 kg of each active substance per hectare. The protective action of the antidote is assessed in percent 20 days after application. Reference values are provided by plants treated with the herbicide alone and by completely untreated control plants. The results are summarised in the following Table.

TABLE 2

| Compound No. | Relative protective action in percent |
|---|---|
| 1 | 50 |
| 3 | 50 |

Example 39

Post-emergence application of herbicide and safener (antidote) as a tank mixture Plastic pots (upper diameter 7 cm) are filled with sandy-clayey loam soil. Wheat seeds of the "Besso" variety are sown therein, covered with soil and subsequently watered. The plants are grown in a greenhouse until they have reached the 2- to 3-leaf stage. The substance to be tested as safener is dissolved in water, and is sprayed together with the herbicide, 2-[4-(3,5-dichloropyridyl-2-oxy)-phenoxy]-propionic acid-2-propynyl ester, onto the plants in a total amount of 550 liters of liquor per hectare. The applied amount of safener corresponds to 1.5 kg per hectare, and the amount of herbicide to 0.75 kg per hectare. The protective action of the safener is assessed in per cent three weeks after application. Reference values are provided by plants treated with the herbicide alone and by completely untreated control plants. The results are summarised in the following Table.

TABLE 3

| Compound No. | Relative protective action in percent |
|---|---|
| 1 | 75 |
| 2 | 63 |
| 4 | 38 |
| 5 | 38 |
| 8 | 38 |

Example 40

Post-emergence application of herbicide and safener (antidote) as a tank mixture Plastic pots (upper diameter 11 cm, content 500 cm³) are filled with sandy-clayey loam soil. Wheat seeds of the "Besso" variety are sown therein, covered with soil and subsequently watered. The plants are grown in a greenhouse up to the 2- to 3-leaf stage. The substance to be tested as safener is dissolved in water, and is sprayed together with the herbicide, 2-[4-(3,5-dichloropyridyl-2-oxy)-phenoxy]-propionic acid-2-propynyl ester, onto the plants in a total amount of 550 liters per hectare. The protective action of the safener is assessed in percent three weeks after application. Reference values are provided by plants treated with the herbicide alone and by completely untreated control plants. The results are summarised in the following Table.

TABLE 4

| Compound No. | Safener kg of a.i.* per ha. | Herbicide kg of a.i. per ha. | Relative protective action in percent |
|---|---|---|---|
| 1 | 1.0 | 1.0 | 75 |
| 1 | 0.5 | 1.0 | 75 |
| 1 | 0.75 | 0.75 | 75 |
| 1 | 0.38 | 0.75 | 75 |
| 1 | 0.5 | 0.5 | 75 |
| 1 | 0.25 | 0.5 | 62.5 |
| 2 | 1.0 | 1.0 | 62.5 |
| 2 | 0.5 | 1.0 | 62.5 |
| 2 | 0.75 | 0.75 | 37.5 |
| 2 | 0.38 | 0.75 | 37.5 |
| 2 | 0.5 | 0.5 | 12.5 |
| 2 | 0.25 | 0.5 | 25 |

*a.i. = active ingredient

Example 41

Post-emergence application of herbicide and safener (antidote) as a tank mixture Plastic containers (length×width×height=25×17×21 cm) are filled with sandy-clayey laom soil. Wheat seeds of the "Besso" variety are sown therein, covered with soil and subsequently watered. The plants are cultivated in a greenhouse up to the 2- to 3-leaf stage. The substance to be tested as safener, 5-chloro-8-(2-butenyloxy)-quinoline (compund No. 1), is then dissolved in water and sprayed together with the herbicide, 2-[4-(3,5-dichloropyridyl-2-oxy)-phenoxy]-propionic acid-2-propynyl ester, onto the plants in a total amount of 550 liters of liquor per hectare. The protective action of the safener is assessed in percent three weeks after application. Reference values are provided by plants treated with the herbicide alone and by completely untreated control plants. The results are summarised in the following Table.

TABLE 5

| Safener kg of a.i. per ha. | Herbicide kg of a.i. per ha. | Relative protective action in percent |
|---|---|---|
| 1.5 | 1.5 | 62.5 |
| 1.5 | 0.75 | 62.5 |
| 1.5 | 0.375 | 62.5 |
| 1.0 | 1.0 | 50 |
| 1.0 | 1.5 | 50 |
| 1.0 | 0.25 | 50 |

What is claimed is:

1. A compound of the formula

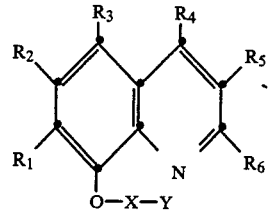

wherein $R_1$, $R_2$ and $R_3$ independently of one another are each hydrogen, halogen, nitro, cyano, $C_1$–$C_8$-alkyl, $C_1$–$C_8$-alkoxy or $C_1$–$C_6$-alkylcarbonyl, $R_4$, $R_5$ and $R_6$ independently of one another are each hydrogen, halogen or $C_1$–$C_8$-alkyl, and (i) X is a $C_1$–$C_4$-alkylene or a $C_2$–$C_3$-alkenylene which is unsubstituted or substituted by chlorine, and Y is chlorine, 2-propenyloxy, dimethylamino, diethylamino, benzyldimethylamino chloride, 1,3-dioxolanyl, methyl-1,3-dioxolanyl, 1,3-dioxanyl, furyl, piperidino, phenyl, chlorophenyl, phenoxy, methylphenoxy, benzyloxy, or acetoxy, or (ii) Y is hydrogen, and X and Y together are butyl, octyl, 2-propenyl, chloro-2-propenyl, 2-butenyl, or 2-propynyl, provided that when X is $C_1$-alkylene, Y is not chlorophenyl, and when X is —CH₂—CH₂— and $R_2$ is methoxy, Y is not diethylamino.

2. A compound according to claim 1, wherein $R_1$ is hydrogen, chlorine or bromine, $R_2$, $R_4$ and $R_5$ are hydrogen, $R_3$ is hydrogen, chlorine, bromine or nitro, $R_6$ is hydrogen or methyl.

3. A compound according to claim 2, wherein (i) X is methylene and Y is 1,3-dioxolan-2-yl, or (ii) X is 2-chloro-2-propenylene, and Y is chlorine, or (iii) Y is hydrogen, and X and Y together are n-butyl, n-octyl or 2-butenyl.

4. A compound according to claim 1, wherein $R_1$ and $R_3$ independently of one another are each hydrogen or chlorine, $R_2$, $R_4$ and $R_5$ are hydrogen, $R_6$ is hydrogen or methyl, X is methylene, and Y is 1,3-dioxolan-2-yl, 1,3-dioxolan-4-yl, 2-methyl-1,3-dioxolan-4-yl, 1,3-dioxan-2-yl, 2-furyl, phenyl or 4-chlorophenyl.

5. A compound according to claim 1, wherein $R_1$ and $R_3$ independently of one another are each hydrogen, chlorine or bromine, $R_2$, $R_4$, $R_5$ and $R_6$ are hydrogen, X is ethylene or trimethylene, and Y is 2-propenyloxy, dimethylamino, diethylamino, benzyldimethylammonio chloride, piperidino, phenoxy, 4-methylphenoxy, benzyloxy or acetoxy.

6. A compound according to claim 1, wherein $R_1$, $R_2$, $R_4$, $R_5$ and $R_6$ are hydrogen, $R_3$ is chlorine, and (i) X is 2-propenylene and Y is phenyl, or (ii) X is 2-butenylene and Y is chlorine.

7. A compound according to claim 1, wherein $R_1$, $R_2$, $R_4$, $R_5$ and $R_6$ are hydrogen, $R_3$ is chlorine, and Y is hydrogen, and X and Y together are n-butyl, sec-butyl, 2-propenyl, 2-chloro-2-propenyl, 2-butenyl or 2-propynyl.

8. A compound according to claim 1 wherein Y is hydrogen and X and Y together are 2-butenyl.

9. A compound according to claim 1, selected from the group consisting of: 8-allyloxyquinoline, 8-(2-butenyloxy)-quinoline, 5-chloro-8-allyloxyquinoline, 5-chloro-8-propargyloxyquinoline, 5-chloro-8-(2-butenyloxy)-quinaldine, 8-octyloxyquinoline, 5-chloro-8-octyloxyquinoline, 8-octyloxyquinaldine, 5-chloro-8-octyloxyquinaldine, 8-(1,3-dioxolan-2-ylmethoxy)-quinoline, 5-chloro-8-(1,3-dioxolan-2-ylmethoxy)-quinoline, 8-(1,3-dioxan-2-ylmethoxy)-quinoline, 5-chloro-8-(1,3-dioxan-2-ylmethoxy)-quinoline and 5-chloro-8-(tetrahydrofuran-2-ylmethoxy)-quinoline.

10. A compound according to claim 1, which compound is 5-chloro-8-(2-butenyloxy)-quinoline.

11. A composition for the protection of cultivated plants against the harmful phytotoxic effects of agricultural chemicals, consisting essentially of an active ingredient compound of the formula

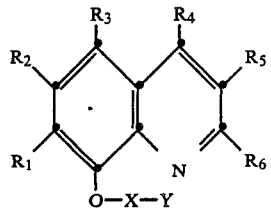

wherein $R_1$, $R_2$ and $R_3$ independently of one another are each hydrogen, halogen, nitro, cyano, $C_1$–$C_8$-alkyl, $C_1$–$C_8$-alkoxy or $C_1$–$C_6$-alkylcarbonyl, $R_4$, $R_5$ and $R_6$ independently of one another are each hydrogen, halogen or $C_1$–$C_8$-alkyl, and (i) X is a $C_1$–$C_4$-alkylene or a $C_2$–$C_3$-alkenylene which is unsubstituted or substituted by chlorine, and Y is chlorine, 2-propenyloxy, dimethylamino, diethylamino, benzyldimethylamino chloride, 1,3-dioxolanyl, methyl-1,3-dioxolanyl, 1,3-dioxanyl, furyl, piperidino, phenyl, chlorophenyl, phenoxy, methylphenoxy, benzyloxy, or acetoxy, or (ii) Y is hydrogen, and X and Y together are butyl, octyl, 2-propenyl, chloro-2-propenyl, 2-butenyl, or 2-propynyl, provided that when X is $C_1$-alkylene, Y is not chlorophenyl, and when X is —$CH_2CH_2$— and $R_2$ is methoxy, Y is not diethylamino, together with an inert argiculturally acceptable additive.

12. A composition according to claim 11, which composition further contains the agricultural chemical to be antagonized.

13. A composition according to claim 11, which composition contains 0.1 to 99 percent by weight of the active ingredient or of a combination of the active ingredient and the agricultural chemical to be antagonised, and 1 to 99.9 percent by weight of a solid or liquid additive, of which 0 to 25 percent by weight is a surface-active agent (tenside).

14. A composition according to claim 11, which composition contains 0.1 to 95 percent by weight of the active ingredient or of a combination of the active ingredient and the agricultural chemical to be antagonised, 5 to 99.8 percent by weight of a solid or liquid additive, and 0.1 to 25 percent by weight of a tenside.

* * * * *